United States Patent [19]

Stiles

[11] 4,111,847
[45] Sep. 5, 1978

[54] METHANOL SYNTHESIS CATALYST

[75] Inventor: Alvin B. Stiles, Wilmington, Del.

[73] Assignee: E. I. Du Pont de Nemours and Company, Wilmington, Del.

[21] Appl. No.: 413,829

[22] Filed: Nov. 8, 1973

Related U.S. Application Data

[63] Continuation-in-part of Ser. No. 245,902, Apr. 20, 1972, abandoned.

[51] Int. Cl.$^2$ .................. B01J 21/04; B01J 21/10; B01J 23/06; B01J 23/72
[52] U.S. Cl. ................... 252/463; 252/475; 260/449.5
[58] Field of Search .............. 252/463, 468, 475; 260/449.5

[56] References Cited

U.S. PATENT DOCUMENTS

| 1,908,696 | 5/1933 | Dodge | 260/449.5 |
|---|---|---|---|
| 2,061,470 | 11/1936 | Larson | 260/449.5 X |
| 3,326,956 | 6/1967 | Davies et al. | 252/468 X |
| 3,689,575 | 9/1972 | Tarhan | 260/449.5 X |
| 3,790,505 | 2/1974 | Casey et al. | 252/463 |
| 3,961,037 | 6/1976 | Davies et al. | 252/463 X |

FOREIGN PATENT DOCUMENTS 7,574/1971  2/1971  Japan ........................ 252/475

*Primary Examiner*—W. J. Shine

[57] ABSTRACT

A catalyst particularly useful in the production of methanol can be made by preparing a solution of copper and zinc nitrates, the ratio of copper to zinc being from 1:1 to 8:1 and then precipitating the copper and zinc by the addition of ammonium carbonate or ammonium bicarbonate. After the precipitated material has been agglomerated and calcined, a copper oxide-zinc oxide catalyst, low in sodium and sulfur is obtained.

4 Claims, No Drawings

METHANOL SYNTHESIS CATALYST

CROSS-REFERENCE TO RELATED APPLICATIONS

This application is a continuation-in-part of my copending application Ser. No. 245,902, filed Apr. 20, 1972, now abandoned.

BACKGROUND OF THE INVENTION

For many years, zinc oxide-chromium oxide catalysts have been employed for methanol synthesis. Recently, copper oxide-zinc oxide mixtures have also been used as methanol synthesis catalyst. Examples of such catalysts can be found in Belgian Patent 743,652, U.S. Pat. Nos. 3,326,956 and 3,514,261.

SUMMARY OF THE INVENTION

I have discovered that improved methanol synthesis catalysts having increased productivity can be made from a solution of copper and zinc nitrates, the ratio of copper to zinc being from 1:1 to 8:1, by precipitating the zinc and copper as carbonates by the addition of ammonium carbonate or ammonium bicarbonate or both. The precipitated carbonates are then further processed, to include calcining, to produce a copper oxide-zinc oxide catalyst containing less than 100 ppm of sodium or sulfur.

The novel catalyst of the invention can be used for methanol production at lower temperatures and pressures than the catalysts commercially available at the present time. Furthermore, these catalysts also improve the economics of methanol production by reducing the formation of byproducts during synthesis.

DESCRIPTION OF THE INVENTION

The novel copper oxide-zinc catalyst of the invention has a ratio of copper to zinc of 1:1 to as high as 8:1. The preferred ratio is about 4:1. The catalyst does not contain combined chromium or chromium oxide.

It is desirable that the catalyst be free from sodium or sulfur, i.e., contains at most, less than 100 ppm of sodium or sulfur. To accomplish this end, the catalyst is prepared from solution of copper and zinc salts that are free from sodium or sulfate ions. The best method of obtaining such solutions is to use copper and zinc nitrates, exercising care to assure the salts are very low in these impurities.

The solution is heated to temperatures in the range of 30° to 80° C. and then ammonium carbonate, ammonium bicarbonate, or both are added to precipitate the zinc and copper as carbonates; the same care is exercised in assuring very low sodium and sulfate impurity level in the precipitant. The carbonates can be added as solids or as solutions and the amount added should be sufficient to precipitate essentially all the copper and zinc present in the solution; this is accomplished by controlling the pH to 6.8 ± 0.1 at 30° to 80° C. The use of these high purity ammonium carbonates enables the desired low sodium content of the catalyst product to be obtained. The time of precipitation should be long enough so as to avoid problems arising from too rapid gas evolution from the slurry and should not be so slow as to cause an uneconomic consumption of time; roughly, 15 minutes would be the minimum time and several hours would be the maximum. The finished precipitate should not be violently agitated because of degradation of the precipitate structure.

In many instances it is desirable to add a thermal stabilizer to the catalyst. The stabilizer can be coprecipitated with the zinc and copper, e.g., by the addition of aluminum nitrate to the solution of zinc and copper nitrate prior to precipitation, or the zinc and copper carbonates can be precipitated on the stabilizer. In the latter embodiment, the stabilizer can be in the form of a powder or a slurry, e.g., finely divided particles of aluminum hydroxide or alumina hydrate Al(OH)$_3$ in suspension. The zinc and copper are then precipitated onto the finely divided particles.

Useful stabilizers include alumina, zirconia, titania, silica, calcia or magnesia. When these stabilizers are to be coprecipitated with the zinc and copper, they should be added to the solution as water soluble salts that are free from sulfur, i.e., can be added as nitrates, organic salts or complexes such as ethyl silicate. The quantity of stabilizer utilized can be varied as desired to modify the activity of the catalyst or its thermal stability. Increasing the quantity of stabilizer increases its thermal stability, whereas decreasing the quantity increased the ratio of active ingredients, with the result that a unit volume of catalyst is increased in activity. Thus for most catalysts the amount of stabilizer will range from 5 to 65% of the total ingredients, i.e., the active ingredients and the stabilizer. It is recognized that the stabilizer may also impart some promoting action.

After the zinc and copper have been precipitated as their carbonates, with or without a stabilizer, the carbonates are then filtered, washed and then calcined at temperatures of 300° to 500° C., usually 375° to 425° C. to decompose the carbonates to the corresponding oxides. The copper oxide-zinc oxide catalyst can then be particulated, i.e., pelleted, formed into granules, etc.

Alternatively, the uncalcined carbonates can be particulated and then calcined. In a preferred embodiment the material particulated, e.g., pelleted, can contain both calcined and uncalcined material. When uncalcined material is pelleted, upon being calcined it decomposes and imparts additional porosity to the final catalyst.

The catalyst thus prepared is particularly useful for the production of methanol. Thus, the catalyst can be utilized in a methanol convertor wherein synthesis gas, e.g., carbon monoxide, carbon dioxide and hydrogen is converted to methanol at temperatures from 450° to 750° F. and pressures of 300 to 1500 psig or if desired at higher pressures, e.g., 1500 to 6000 psig or even higher, but ordinarily the high pressures are not desired for economic reasons. One of the advantages of the catalyst of the invention is that it can be operated at the lower pressures and temperatures.

In the following examples all parts are parts by weight unless otherwise indicated.

EXAMPLE 1

(1) 75 Parts of zinc nitrate trihydrate, 300 parts of copper nitrate trihydrate and 180 parts of aluminum nitrate nonahydrate are dissolved in 1500 parts of distilled water at 30° C.

(2) As the solution is rapidly agitated, a 10% solution of ammonium bicarbonate is added until a pH of 6.8 ± 0.1 is reached. The flow of ammonium bicarbonate should be adjusted so that the time required for precipitation is about 30 minutes and the temperature is maintained at 30° C.

(3) Agitation is continued for 30 minutes, then the slurry is filtered, washed with 500 parts of distilled water, and the filter cake dried.

(4) After drying the filter cake is calcined at 400° C. for 2 hours after the 400° C. temperature is reached.

(5) After cooling the calcined product, i.e. a powder, is densified by kneading in a sigma type "kneader" using sufficient distilled water to produce a putty-like paste.

(6) The densified paste is dried, then is granulated by passing 100% through a 10 mesh screen.

(7) The powder thus obtained is mixed with 1% powdered graphite and is formed into pills (cylinders ⅛ inches long × ⅛ inch diameter) in a typical pharmaceutical tableting machine. These pills are suitable for use as a catalyst synthesizing methanol from carbon oxides and hydrogen, as subsequently described.

The catalyst derived above is charged to a reactor with provisions for maintaining a constant temperature within the reactor. This can be accomplished by maintaining the reactor in a constant temperature bath of fluidized solids or suitable liquid. Provision is made to allow gas to enter the top of the reactor and be exhausted at the bottom of the reactor. Also, it is so designed that pressure can be varied from atmospheric to 5000 psi.

A mixture of gas comprising 8.8% carbon monoxide, 4.0% carbon dioxide, and 87.2% hydrogen is passed over the catalyst in the reactor after it has been prereduced with 5% hydrogen in nitrogen (anhydrous gas) at 250° C. The reduction procedure is that known in the art and briefly consists in passing the reducing gas (ca. 5% $H_2$ in $N_2$) over the catalyst at a space velocity of 500 to 5000 until reduction is completed as evidenced by the absence of $H_2O$ in the off gas.

The catalyst is exposed to various operating conditions of temperatures, pressure, and space velocity. The results obtained with this catalyst are tabulated subsequently and are identified as A-1.

Instead of using the quantities of salts and water called for in step 1, there is used in addition to the aluminum nitrate salt, 121.7 parts of the zinc salt, 120.8 parts of the copper salt, and 1000 parts of distilled water. This solution is processed as described in steps 1 through 7, and the product is tested in the same manner as with the first catalyst. The results of this test are tabulated in the subsequent tabulation as A-2.

Instead of the ingredients used in step 1 of this example, there is used 270 parts aluminum nitrate nonahydrate with the zinc nitrate trihydrate and copper nitrate trihydrate remaining the same. One-thousand-one-hundred-fifty parts of distilled water is used. This solution is similarly processed and the product tested; the results are tabulated subsequently as A-3.

In another embodiment, the zinc and copper can be precipitated onto water-insoluble finely divided alumina hydrate $Al(OH)_3$. The quantity of alumina hydrate required to be equivalent to the aluminum nitrate stipulated in step 1 above would be 41 parts by weight.

EXAMPLE 2

This example involves a catalyst not within the scope of the invention and is prepared for comparison purpose.

A solution is prepared comprising 480 parts of copper nitrate trihydrate alone with no zinc or aluminum salts and using 2150 parts of distilled water. This solution is rapidly agitated and adjusted to a temperature of 30° C.

This solution is made into a catalyst and tested in exactly the same manner as the catalyst of Example 1, except, of course, step 1 of Example 1 is not used. The results are tabulated subsequently as B-1.

EXAMPLE 3

The catalyst of this example is prepared similar to that of Example 1, with the exceptions that 60 parts of $Zn(NO_3)_2 \cdot 3H_2O$ and 360 parts $Cu(NO_3)_2 \cdot 3H_2O$ are used and in the calcining step described in step 4, only 45% of the dried filter cake is calcined, and the remaining 55% is left uncalcined.

The calcined material and the uncalcined material are kneaded as described in step 5 to produce a dense powder. All other operations of Example 1, including the testing, are performed on this catalyst. The results of testing are also tabulated subsequently as C-1.

Instead of the ratio of 45:55 for the calcined versus uncalcined catalyst, the ratio can be increased or decreased as desired. Increasing the quantity of uncalcined material increases the porosity of the finished catalyst, and consequently its activity per unit volume. There is simultaneously, however, a decrease in physical strength of the catalyst, so that if it becomes necessary to increase the strength above that achieved with the 45:55 ratio, the quantity of uncalcined material is decreased below the 45:55 ratio. Some of the loss in strength can be compensated for by increased pelleting pressure, but the application of increased pressure is limited, and ultimately it may become necessary to change the ratio of uncalcined to calcined material.

A sample C-2 prepared with no uncalcined material is included in the kneader mix. Test data are also tabulated subsequently.

| | | | | | | | | | | | | |
|---|---|---|---|---|---|---|---|---|---|---|---|---|
| TABULATION OF TEST DATA FOR METHANOL SYNTHESIS CATALYSTS PREPARED ACCORDING TO EXAMPLES | | | | | | | | | | | | |
| Catalyst Identification | Ratio of Active Ingredients | | Percent of Uncalcined Material in Kneaded Paste | Stabilizer | | Space Velocity hr$^{-1}$ | Feed Gas-mole % | | | °C Temp | Press lb/in$^2$ | Productivity ml $CH_3OH$ per ml · Catalyst per hr | Quality of Crude MeOH | Byproduct |
| | Zn | Cu | | Type | Weight Ratio to ZnO + CuO | | $H_2$ | CO | $CO_2$ | | | | | |
| A-1 | 1 | 4 | 0 | $Al_2O_3$ | 0.17 | 200 M | 87.2 | 8.8 | 4.0 | 275 | 1000 | 6.0 | Very Good | Low |
| A-2 | 1 | 1 | 0 | $Al_2O_3$ | 0.08 | 50 M | 87.2 | 8.8 | 4.0 | 275 | 1000 | 5.0 | Very Good | Low |
| A-3 | 1 | 4 | 0 | $Al_2O_3$ | 0.27 | 50 M | 87.2 | 8.8 | 4.0 | 275 | 1000 | 4.0 | Very Good | Low |
| B-1 | 0 | | 0 | 0 | 0 | 200 M | 87.2 | 8.8 | 4.0 | 275 | 1000 | 0.1 | Insignificant | Too Low Productivity |
| C-1 | 1 | 6 | 55 | $Al_2O_3$ | 0.17 | 50 M | 87.2 | 8.8 | 4.0 | 275 | 1000 | 5.0 | Very Good | Very Low |
| C-2 | 1 | 6 | 0 | $Al_2O_3$ | 0.17 | 50 M | 87.2 | 8.8 | 4.0 | 275 | 1000 | 5.0 | Very Good | Very Low |
| C-2 | 1 | 6 | 0 | $Al_2O_3$ | 0.17 | 200 M | 87.2 | 8.8 | 4.0 | 275 | 1000 | 8.0 | Very Good | Very Low |

EXAMPLE 4

The following example is offered to illustrate the difference in activity between a copper oxide-zinc oxide catalyst precipitated with ammonium carbonate as compared with one precipitated with sodium carbonate. It should be noted that the catalyst compositions compared are not of the high copper to zinc ratio type of the invention, but rather are 1 copper to 2 zinc ratio catalysts. However, one skilled in the art would expect that similar, possibly even greater, difference in activity would be obtained from a similar comparison of high copper to zinc ratio catalysts, i.e., the sample precipitated with ammonium carbonate would illustrate improved activity of the same or greater magnitude.

SAMPLE A

The procedure used for the preparation of the catalyst precipitated with ammonium carbonate is as follows: 1. A solution is prepared by dissolving 120 parts by weight of copper nitrate trihydrate, 297 parts by weight of zinc nitrate tirhydrate, and 140 parts of aluminum nitrate nonahydrate in sufficient distilled water to make a total of 1500 parts by weight of water and salts combined.

2. Separately, a solution is prepared comprising 84 parts by weight of ammonium carbonate in sufficient distilled water to be equal to 1000 parts, total water and ammonium carbonate.

3. While the solution prepared in Item 1 is rapidly agitated and is controlled at a temperature of 50° C, sufficient ammonium carbonate solution is added over a period of 90 minutes to raise the pH to 6.9.

4. After the pH has reached 6.9, addition is stopped, the temperature is maintained at 50° C for an additional hour, and agitation is continued during this period.

5. After the digestion period, the slurry is filtered, the filter cake is washed with distilled water to remove soluble salts, then the washed filter cake is dried and finally calcined at 400° C for 2 hours.

6. The calcined mixture of oxides is densified by kneading with water, is again dried, and mixed with 1% graphite and formed into ¼ × ¼ inch pellets in a pelleting machine of the type commonly used in the pharmaceutical industry. The catalyst at this point is ready for testing, as described hereinafter.

SAMPLE B

A catalyst is similarly prepared with the exception that it is precipitated with sodium carbonate instead of ammonium carbonate and the precipitate is washed with ammonium carbonate to remove foreign ions such as sodium occluded in the precipitate. The procedure is as follows:

1. A solution is prepared by dissolving 120 parts by weight of copper nitrate trihydrate, 297 parts by weight of zinc nitrate trihydrate, and 140 parts of aluminum nitrate nonahydrate in sufficient distilled water to make a total of 1500 parts by weight of water and salts combined.

2. A solution is prepared comprising 106 parts by weight of sodium carbonate in sufficient distilled water to be equivalent to 1000 parts by weight total of carbonate and water.

3. While the solution prepared in Item 1 is rapidly agitated and is controlled at a temperature of 50° C, sufficient sodium carbonate solution is added over a period of 90 minutes to raise the pH to 6.9.

4 The slurry is digested for 1 hour at 50° C and is then washed, dried, and calcined for 2 hours at 400° C.

5. The calcined powder obtained in item 4 is slurried in 1000 parts by weight of 0.1% ammonium bicarbonate solution.

6. The slurry is allowed to settle and the supernatant liquid is decanted so that 75% of the liquid is removed. Additional ammonium carbonate solution is added to bring the volume back to the volume initially obtained for the slurry.

7. The washing by decantation is repeated until four decantations have been performed.

8. The washed slurry is filtered, the filter cake dried, and eventually converted to pellets as described for Sample A, above. There are thus produced two catalysts, one of which has been precipitated with ammonium carbonate and the other precipitated with sodium carbonate, with supplementary washings being performed on that precipitated with sodium carbonate to reduce the sodium level to below 500 ppm.

Evaluation of Catalysts of Samples A and B

Both samples were tested simultaneously in two parallel test reactors operating at 1000 psi at 275° C, and a space velocity of 200,000 and with a hydrogen to carbon oxide ratio of 6.7. The carbon oxides comprise approximately 75% carbon monoxide and 25% carbon dioxide.

Under these conditions, Sample A produced methanol at a rate described arbitrarily at 51 and continued for 6 days at a rate in excess of 38. Simultaneously, Sample B was evaluated and initially gave activity of 38 and after six days this had dropped to 33. Both catalysts appeared to be leveling out at these final rates.

It can be concluded from the above that precipitation with ammonium carbonate in preference to sodium carbonate produces a catalyst which is initially more active than that precipitated with sodium carbonate, and after 6 days and a period of stable activity has been reached, the catalyst precipitated with ammonium carbonate is stabilizing at a rate approximately 15% above that of the catalyst produced by precipitation with sodium carbonate.

In industrial practice, 15% activity differential is valuable and its value can be illustrated by the fact that many catalysts are removed from service when they have decreased by 15 to 20% from the activity they originally demonstrated.

I claim:

1. A copper oxide-zinc oxide catalyst useful for the production of methanol prepared by (a) coprecipitating zinc and copper carbonates from an aqueous solution of the metal nitrates containing very low amounts of sodium and sulfate ions using ammonium carbonate, bicarbonate or mixtures thereof as the sole precipitant by controlling the pH at about 6.8 at a solution temperature in the range of 30° to 80° C. and (b) drying and calcining the resultant coprecipitate at a temperature in the range of 375° to 425° C. to form the oxides of the metals, the sodium and sulfur contents of the calcined catalyst each being less than 100 ppm and the atomic ratio of copper to zinc being from 1:1 to 8:1, said catalyst having incorporated in it 5 to 65% by weight of the total ingredients of a stabilizer selected from alumina, zirconia, titania, calcia or magnesia.

2. The catalyst of claim 1 wherein a portion of the precipitated materials are calcined and then recombined with the uncalcined portion, particulated and the particulated mixture calcined.

3. The catalyst of claim 1 wherein the precipitated materials are calcined prior to being particulated.

4. The catalyst of claim 1 in which the stabilizer is incorporated into the catalyst by coprecipitation of a salt thereof from said aqueous solution.

* * * * *